United States Patent [19]

Karapita

[11] Patent Number: 4,736,922
[45] Date of Patent: Apr. 12, 1988

[54] SUSPENSION SYSTEM

[76] Inventor: Alexander D. Karapita, 38 Robinter Dr., Willowdale, Ontario, Canada, M2M 3R2

[21] Appl. No.: 869,699

[22] Filed: Jun. 2, 1986

Related U.S. Application Data

[63] Continuation-in-part of Ser. No. 602,316, Apr. 20, 1984, Pat. No. 4,645,156.

[30] Foreign Application Priority Data

Jun. 3, 1985 [GB] United Kingdom ............... 8513899

[51] Int. Cl.⁴ .............................................. A47H 1/10
[52] U.S. Cl. .................... 248/325; 248/280.1; 248/648; 248/662
[58] Field of Search ............... 248/648, 661, 662, 665, 248/280.1, 281.1, 292.1, 325, 326, 324; 362/384, 401, 428; 378/190, 193

[56] References Cited

U.S. PATENT DOCUMENTS

| | | | |
|---|---|---|---|
| 1,758,469 | 5/1930 | Sansburn | 362/401 X |
| 2,837,307 | 6/1958 | Schwager et al. | 248/325 |
| 3,065,332 | 11/1962 | Lauterbach | 362/401 |
| 3,615,067 | 10/1971 | Goudreau | 248/325 |
| 3,751,654 | 8/1973 | Grebinar | 362/401 |
| 4,032,775 | 6/1977 | Bobrick | 248/326 X |
| 4,408,740 | 10/1983 | Kleber | 248/661 X |
| 4,421,450 | 12/1983 | Kouno | 248/325 X |
| 4,591,122 | 5/1986 | Kreuzer | 248/280.1 |

FOREIGN PATENT DOCUMENTS 2141461 6/1979 Fed. Rep. of Germany ...... 378/190

Primary Examiner—J. Franklin Foss
Attorney, Agent, or Firm—Sim & McBurney

[57] ABSTRACT

Apparatus for suspending an article for movement in a gravitational field incorporates a fixed hanger with one or more axle members stacked below the hanger and connected thereto. For each axle there is a rotor mounted on the axle, with a housing connected to the rotor and defining a horizontal passageway offset with respect to the rotational axis of the rotor. In each passageway there is a slide arm, and a guiding mechanism for guiding the slide arm. In a preferred form, the slide arm defines a horizontal axis about which a swing arm is pivoted, the swing arm supporting an article at the other end. A constant force is generated within the apparatus, and the force is applied to the swing arm in such a way as to consistently counterbalance the weight of the article.

29 Claims, 12 Drawing Sheets

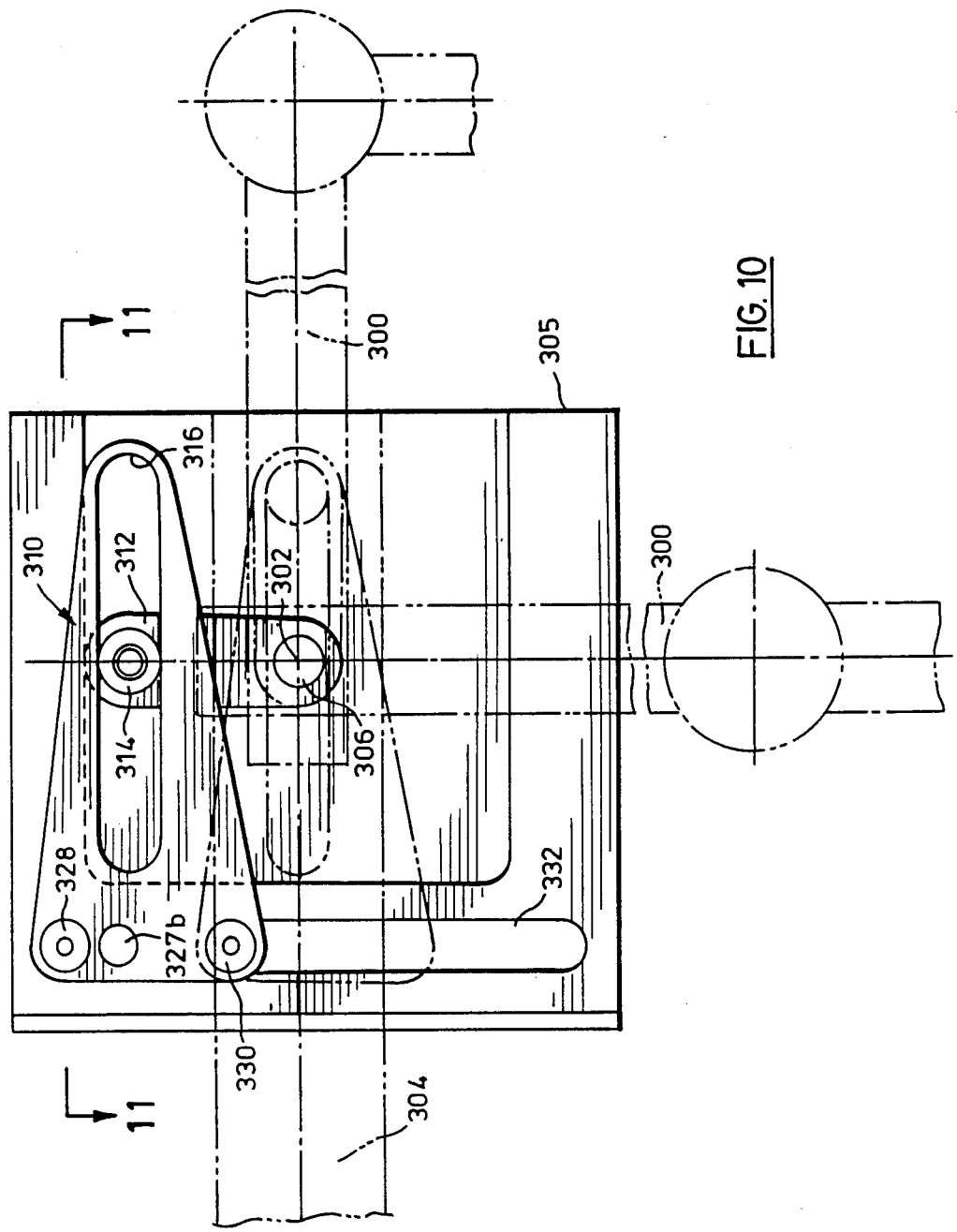

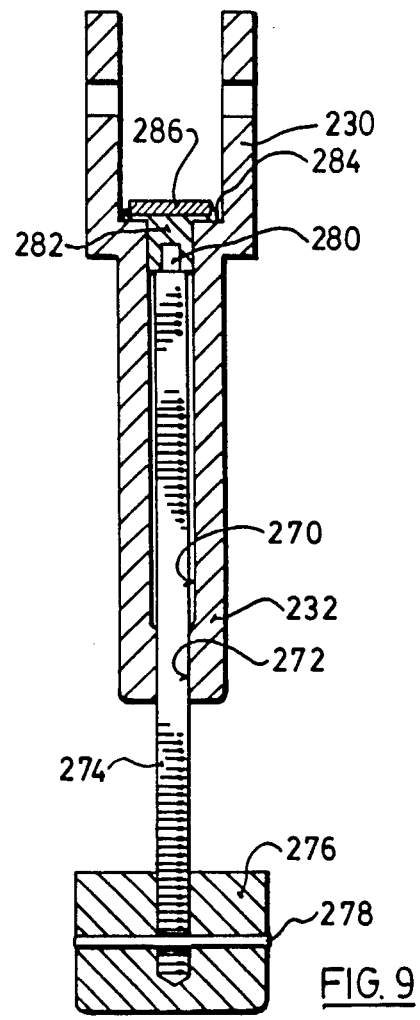
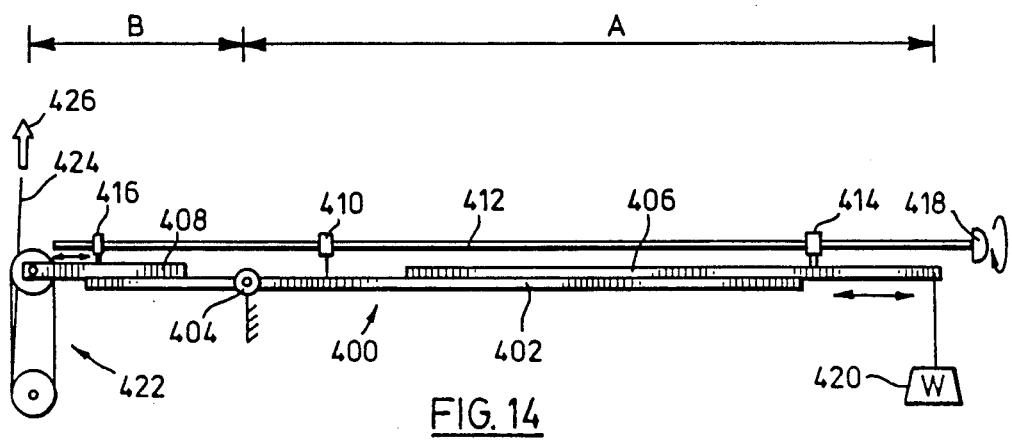

SUSPENSION SYSTEM

This is a continuation-in-part of U.S. patent application Ser. No. 602,316, filed Apr. 20, 1984, now U.S. Pat. No. 4,645,156.

This invention relates to a suspension system for suspending articles for movement in the vertical, horizontal and rotational sense, and has to do particularly with a system capable of not only suspending the articles, but feeding gas, electrical and other lines to the articles in an unobtrusive manner.

BACKGROUND OF THIS INVENTION

One area of particular suitability for the apparatus to be described herein relates to hospital practice, although it is emphasized that this apparatus can find use in many other environments as well. No limitation to hospital practice is implied.

With the greatly increased use of monitoring equipment in hospitals, there is a considerable need for an apparatus capable of suspending pieces of equipment in such a way that the equipment can be manipulated to different positions in use. For example, it may be required to have a piece of apparatus for testing blood pressure readily available for use with a patient, but easily maneuvered into a position where it is not in the way of other treatment when not in use. There is also a requirement for suspending intravenous feeding equipment that varies depending upon circumstances, thus requiring the equipment to be movable with respect to the patient.

Adjustable suspension apparatus for these purposes is available, but it tends to be cumbersome and relatively inconvenient to use. Currently available equipment consists of a series of horizontally disposed arms pivotally connected at their ends by vertically extending pins, so that they can be disposed at various angles towards each other to permit the projection of the end of the free arm to a desired location. The arrangement is flimsy and the mechanical design is difficult from a strength point of view at the vertically extending pins. The use of more than one arm in a particular application is particularly cumbersome.

GENERAL DESCRIPTION OF THIS INVENTION

The general aim of the present invention is to provide an apparatus from which equipment of the above-mentioned kind can be suspended, the apparatus being easier to manipulate and avoiding the cumbersome nature of the prior devices, especially in those cases where there is a requirement to suspend apparatus from more than one support arm.

It is an aim of a further aspect of this invention to provide apparatus as defined immediately above, capable of providing electrical, gas and other feed lines to a point of availability, in an unobtrusive and uncluttered manner.

More particularly, this invention provides an apparatus for suspending an article for movement in the gravitational field, including hanger means adapted to be fixed in place, an axle member below and secured to the hanger means, a rotor portion mounted on the axle member for rotation about a vertical axis, and a housing connected to the rotor portion and defining a horizontal passageway offset with respect to the vertical axis. A slide arm is located in the passageway, and the apparatus includes guide means for guiding the slide arm within the passageway.

As an alternative embodiment, the apparatus can include a plurality of axle members and associated rotor portions in vertically stacked arrangement, as defined above, each rotor portion having a housing in which a slide arm is slidable.

This invention further provides an apparatus for counterbalancing the weight of an article in the gravitational field while allowing the article to be displaced vertically. The apparatus incorporates a first member defining a horizontal axis, and a swing arm pivoted adjacent one end about the horizontal axis and having support means adjacent the other end for supporting the article. The apparatus includes first means providing a substantially constant force, and second means applying that force to the swing arm at a given location spaced from the horizontal axis, so as to maintain a substantially constant proportion between (a) the horizontal distance between the axis and a vertical line through the article, and (b) the distance from the axis to a line parallel to the direction of the force and passing through the said location, the latter distance being taken normal to said last-mentioned line.

GENERAL DESCRIPTION OF THE DRAWINGS

Two embodiments of this invention are illustrated in the accompanying drawings, in which like numerals denote like parts throughout the several views, and in which:

FIG. 9 is a vertical section through a brake-applying mechanism forming part of the device of FIG. 6;

FIG. 10 is an elevational view of a further embodiment the device of FIG. 6, adapted for 360° swivelling with compensation;

FIG. 14 is a schematic view showing a compensated swing arm of which the effective length is variable, the torque compensation being unaffected by the change in length.

DETAILED DESCRIPTION OF THE DRAWINGS

Figure 1:
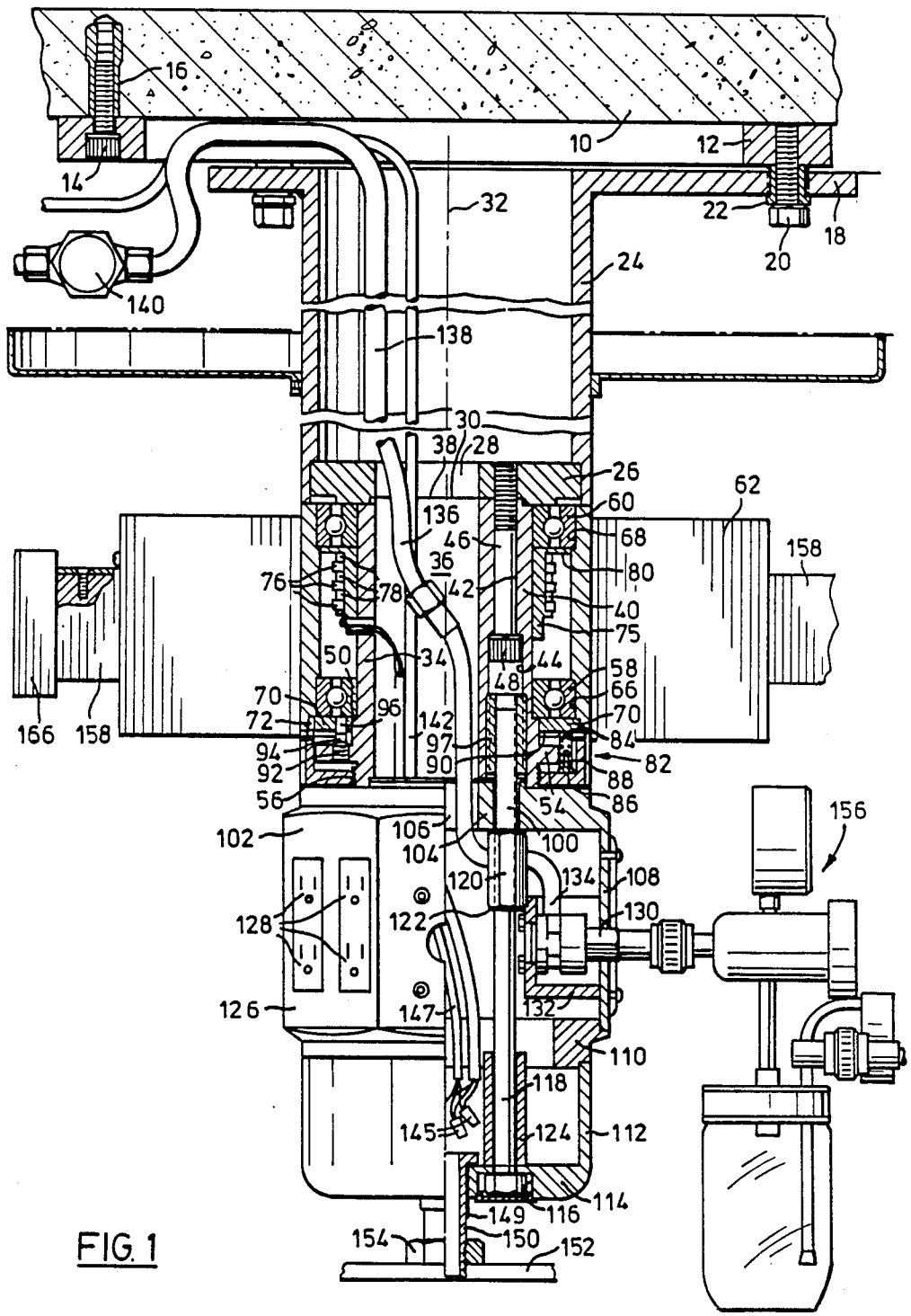
FIG. 1 is an axial sectional view of an apparatus constructed in accordance with this invention, taken in the vertical plane, with a minor portion of the apparatus being shown in elevation.

FIG. 1 shows at the top a poured concrete ceiling 10 to which an anchor ring 12 is securely mounted by a plurality of cap screws 14 embedded in lead anchors 16 within the concrete. Typically, twelve cap screws 14 could be used, spaced around the anchor ring 12. Affixed to the anchor ring 12 is a triangular plate 18, the securement being by way of three cap screws 20 threaded into respective leveller screws 22, which are in turn threaded through the plate 18. Welded to the plate 18 is a cylindrical, hollow hanger tube 24, to the bottom of which is welded an end plug 26 having a three-lobed opening 28, through which gas, electrical and other lines can pass. The bottom of the end plug has a circular recess 30 concentric with the main axis 32 of the hanger tube 24 and the end plug 26.

A hollow axle 34, also having a three-lobed central opening 36, is constructed to provide a circular raised portion 38 adapted to register in the recess 30, with the outside diameter of the axle 34 being somewhat greater than the diameter of the portion 38. This registry ensures concentricity between the axle 34 and the end plug 26.

The three-lobed central opening in both the axle 34 and the end plug 26 leaves three thickened regions, of which one, identified by the numeral 40, is cut by the section of FIG. 1. Each thickened portion 40 of the axle 34 is drilled to provide a bore 42 having a lower portion 44 of increased diameter, the portion 44 being internally threaded at its lower end. The end plug 26 has, for each bore 42, a threaded bore 45 adapted to receive the threads of a housing attachment screw 46, the head 48 of the screw 46 bearing against a lock washer in turn bearing against the shoulder between the bore 42 and the portion 44 of increased diameter. The three screws 46 thus secure the axle 34 in place with respect to the end plug 26.

The axle 34 has an upwardly facing shoulder 50 near its lower end, and below the shoulder 50 is a widened portion 52 from which outwardly extends a flange 54. At the bottom, the axle 34 is threaded at 56 for a purpose to be described subsequently.

A first deep-grooved bearing 58 surrounds the axle 34 and abuts the shoulder 50. A second bearing 60 has a tight fit around the axle 34 near the upper end thereof.

A main housing 62 having an axis offset from the axis 32 of the axle 34 is integral with a rotor portion 64, which coaxially surrounds the axle 34 and engages the outer races of the bearings 58 and 60. More particularly, the rotor portion 64 is machined to provide a lower recess 66, and an upper recess 68, the recesses 66 and 68 receiving the bearings 58 and 60, as best seen in FIG. 1. Thus it can be seen that any axial load on the main housing 62 tending to move the housing 62 downwardly with respect to the axle 34 will be resisted primarily by the lower bearing 58, due to the inside and outside shoulders with which it is in contact.

A housing ring 70 is fastened to the rotor portion 64 by a plurality of set screws 72 securely threaded into a plurality of threaded bores having their axes at the outer cylindrical surface of the ring 70, so that they are threaded partly into the rotor portion 64 and partly into the ring 70. This secures the ring 70 in place with respect to the rotor portion 64.

A cylindrical commutator housing 75 is mounted concentrically around the outside of the axle 34 just below the upper bearing 60, and supports three commutator slip rings 76 which are separated by spacers 78. The commutator housing 75 includes an upper flange 80 with an undercut to prevent bearing oil from reaching the slip rings 76.

Shown to the right of axis 32 in FIG. 1 is a braking mechanism 82, which includes a cartridge 84 of friction material which is vertically slidable in a bore drilled through the flange 54. A push rod 86 supports the lower end of a compression spring 88 which seeks to push the rod 86 and the cartridge 84 away from each other, thus urging the cartridge 84 upwardly into and against a recess 90 in the lower undercut surface of the ring 70. In the preferred embodiment, there are three of the mechanisms 82 provided in the flange 54, spaced at 120° from each other.

Shown to the left of the axis 32 in FIG. 1 is a stop member 92 having a lower threaded end which is threadably engaged with the flange 54 at a shorter radial distance from the axis 32 than the mechanism 82, so that there is no rotational interference. The stop member has an upwardly projecting portion 94, which is positioned to encounter mechanical interference with a pin 96 which is press-fitted into the ring 70 to project downwardly therefrom. The flange 54 has a plurality of bores into which one or two of the pins 96 can be fitted, in order to limit the rotational arc of the main housing 62 with respect to the axle 34.

The widened portion 44 of the bore 42 is threaded at its lower part to receive a thread coupler 97 which is adapted to receive the threaded shaft of either another attachment screw identical to the screw 46, or the end of a threaded stud. In the embodiment shown, a threaded stud 100 is provided, because of the nature of the part to be attached below the axle 34. It will be understood from what follows, however, that another axle identical to axle 34 (and the various parts connected thereto) could be attached directly under the axle 34 shown at the top in FIG. 1.

In the embodiment illustrated, a shroud 102 is provided, the shroud having an upper wall 104 defining a three lobed recess 106 registering with the recess 36, a side wall 108 integral with the top wall 104, and a bottom cap 110 configured to register with the lower edge of the side wall 108.

A cup member 112 extends downwardly from the bottom cap 110, and includes a lower wall 114 having three recesses 116 for receiving the heads of three lower studs 118, the latter being long enough to engage the bottoms of respective coupler nuts 120 which are threaded to the bottom of the respective studs 100. Lock washers 122 are provided above the nuts 120, and it will be appreciated that the shroud 102 is held in place by the nuts 120. The cup member 112 is held in place by the studs 118. Around each of the studs 118 is provided a cylindrical spacer 124.

The side wall 108 of the shroud 102 is octagonal in configuration, and in the embodiment illustrated four of the sides, including the side 126 seen at the left of FIG. 1, each have four electrical plug outlets 128, making sixteen in all.

The other four faces of the octagonal side wall of the illustrated embodiment each have provision for a quick-connect medical gas outlet 130 of known construction. As seen at the right in FIG. 1, a mounting bracket 132 supports the outlet 130. A gas line 134 feeds the outlet 130, and is in turn connected through gas conduit 136 to a main feeder 138. The feeder 138 has a valve 140 to control the gas supply. Thus, facility is available for four different gases through four faces of the octagonal side wall 108. It will be understood, however, that additional faces could be provided for gas or electrical outlets.

The electrical outlets are fed from an electrical wire 142, both the wire 142 and the gas line passing through the three-lobed openings in the axle 34 and the top wall 104 of the shroud 102.

Electrical connection is also made from the electrical wire 142, through the wire connectors 145, and along the commutator wires 147 to the slip rings 76.

At the bottom centre of the cup member 112, a nylon bushing 149 supports a swivel stem 150 on which is threaded a monitor bracket partly shown at 152, and a lock nut 154.

The numeral 156 generally designates gas-using apparatus, which forms no part of this invention.

Figure 2:
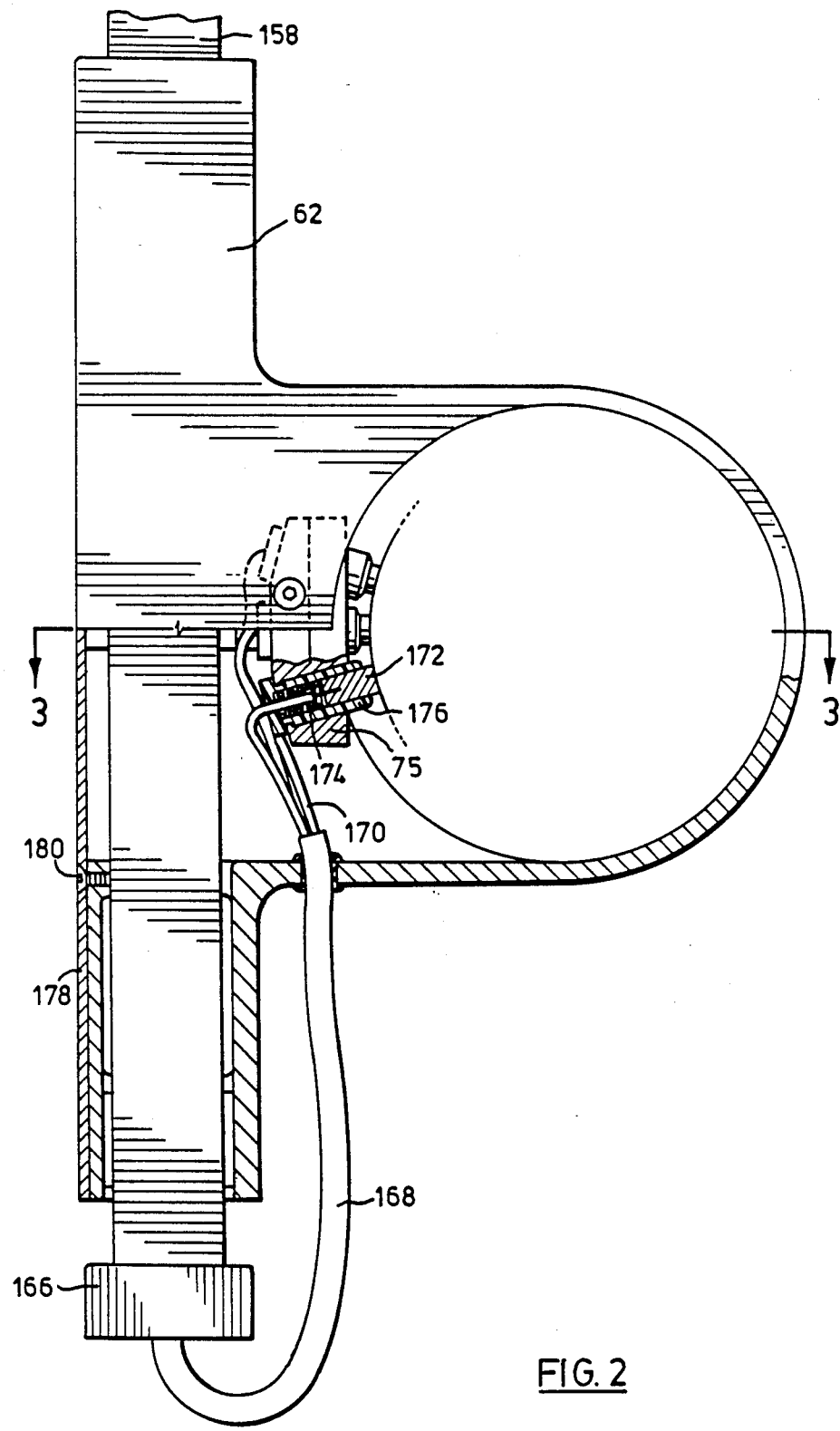
FIG. 2 is a sectional view taken at the line 2—2 in FIG. 1.
Figure 3:
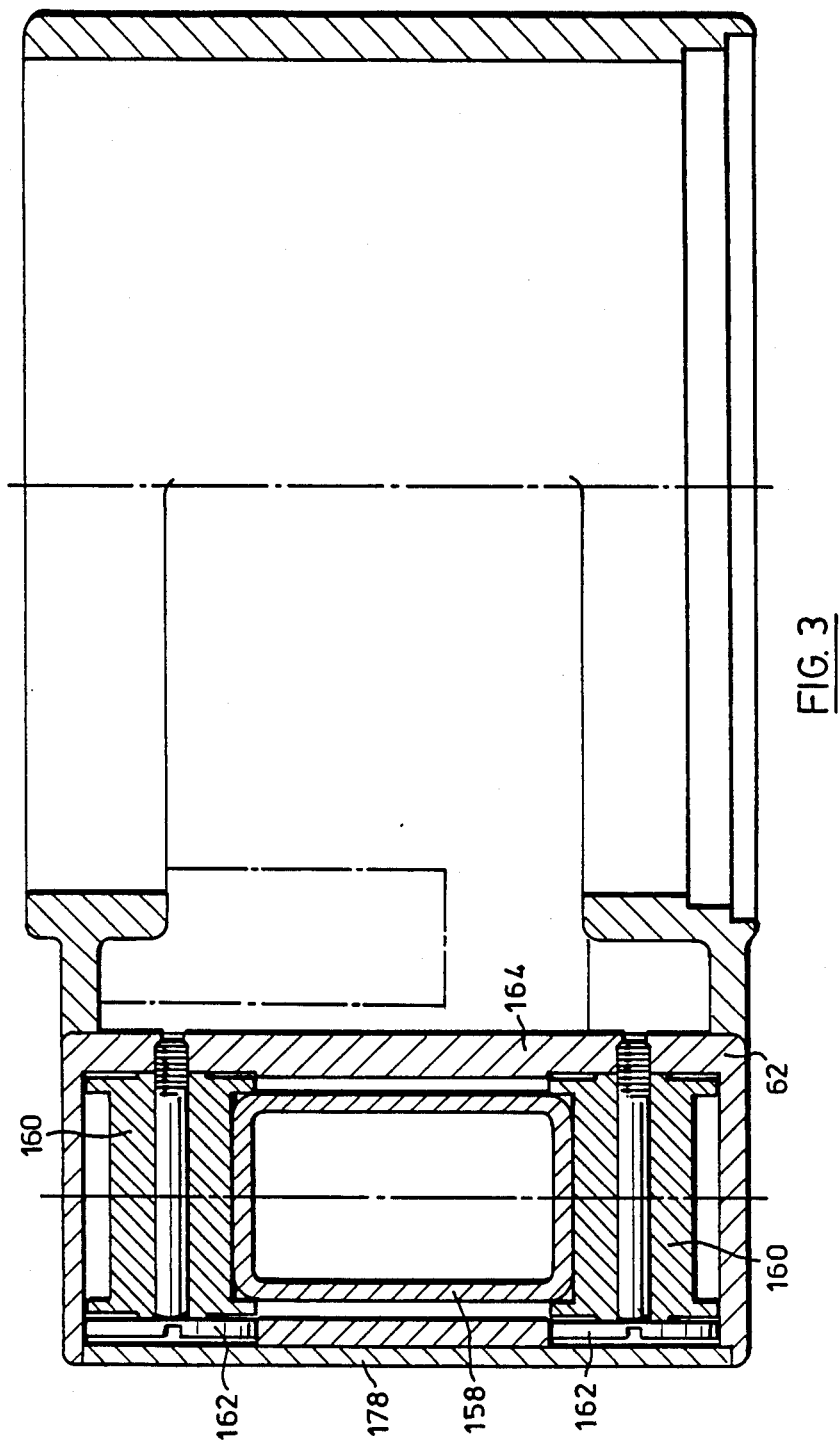
FIG. 3 is a sectional view taken at the line 3—3 in FIG. 2.

Attention is now directed to FIGS. 1, 2 and 3, which clearly show that the main housing 62 is offset from the axis 32 of the axle 34, and that the main housing 62 has provision for a longitudinally slidable primary arm 158 which is adapted to slide on four rollers 160, these being disposed two at either end of the housing 62, above and below the arm 158. The rollers are secured in position by large-head fasteners 162, which are threaded into the righthand wall 164 of the main housing 62, as pictured in FIG. 3.

The rollers 160 are separated by a substantial distance in order to distribute the load and facilitate rolling. Advantageously, the rollers 160 can be made from a material sold under the designation Delrin AF100, which has low static and dynamic friction coefficients. The coefficients are almost identical, thus avoiding the stick-slip problems inherent in other roller materials. This also avoids the problem of galling, which arises when metal rolls on metal.

The arm 158 has an end cap 166, through which electrical wires surrounded by a protective sheath 168 can pass to the interior of the arm 158, to power various items at the opposite end of the arm, as will be subsequently described.

The wires are shown in FIG. 2 at 170, there being three wires in the embodiment illustrated, each wire having its bared end electrically connected to a graphite commutator contact 172, which is urged rightwardly (in FIG. 2) against its respective slip ring by the action of a compression coil spring 174 held within an insulating contact housing 176 which is threaded into the commutator housing 75. A cover plate 178 for the main housing is held in place by machine screws 180 (see FIG. 2). In order to have access to the commutator rings and the contacts, the arm 158 is removed from the housing 62, and the cover plate 178 is taken off the housing 62.

As an alternative to the slip rings and commutator contacts, it would be possible to provide a conduit loop located between the axle 34 and the rotor portion 64, with the conduit loop being directly connected between the wires 170 and the main central electrical wire 142. This avoids any irregularity in the power signal due to movement of contacts on the slip rings. The conduit loop would extend loosely in the space between the axle 34 and the rotor portion 64, and would be long enough to allow complete rotation of the rotor portion 64 about the axle 34, to all possible positions.

Figures 4, 5:
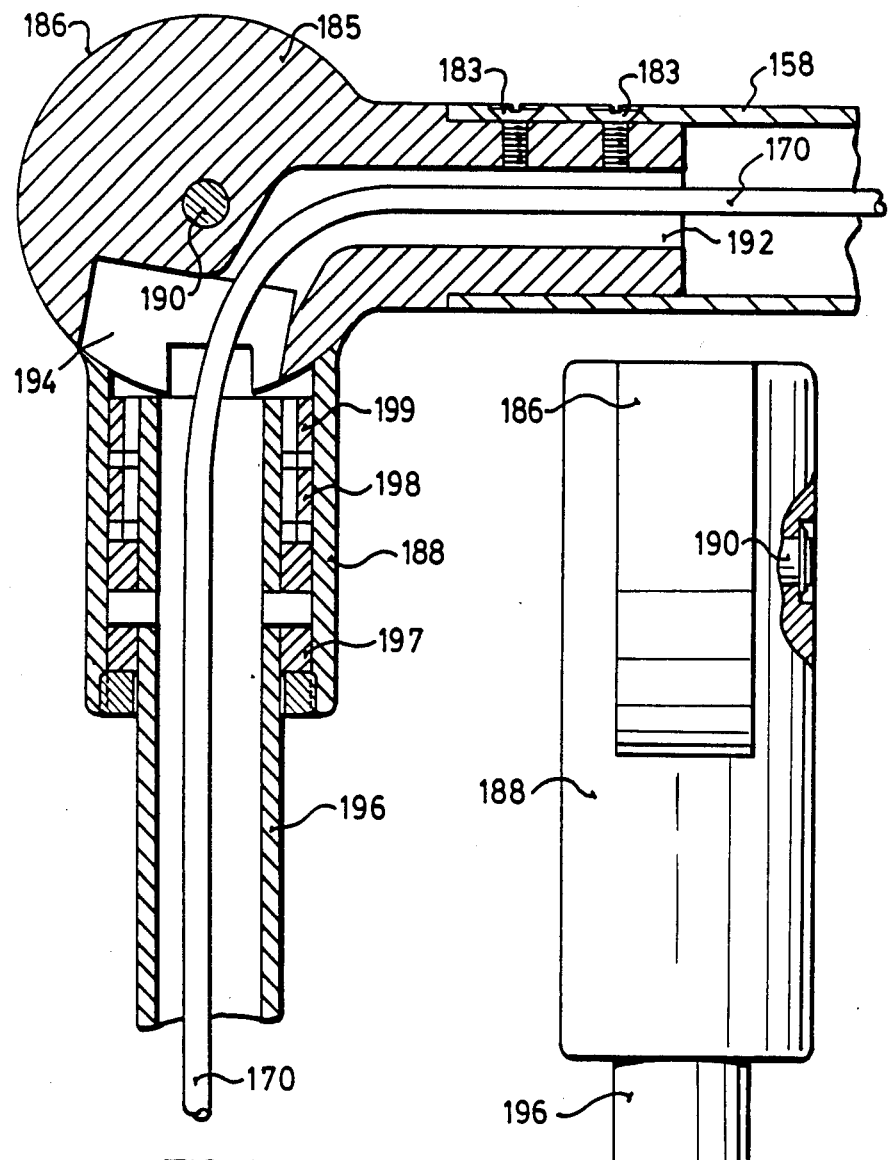
FIG. 4 is a sectional view taken longitudinally through a swivel end of a support arm.
FIG. 5 is an elevational end view of the portion shown in FIG. 4.

Attention is now directed to FIG. 4, which shows the opposite end of the primary arm 158. The arm 158 is connected by machine screws 183 to a flex head 185 defining a cylindrical portion 186 at the leftward end in FIG. 4. The cylindrical portion 186 is received within a yoke member 188 and pivoted thereto by a flex head pin 190. The electrical wire 170 passes through a central passageway 192, thence into a recess 194, and thence into the centre of a hanger tube 196. The hanger tube 196 is supported by the yoke member 188 for limited rotation, by virtue of lost-motion sleeves 197, 198 and 199.

Figure 6:
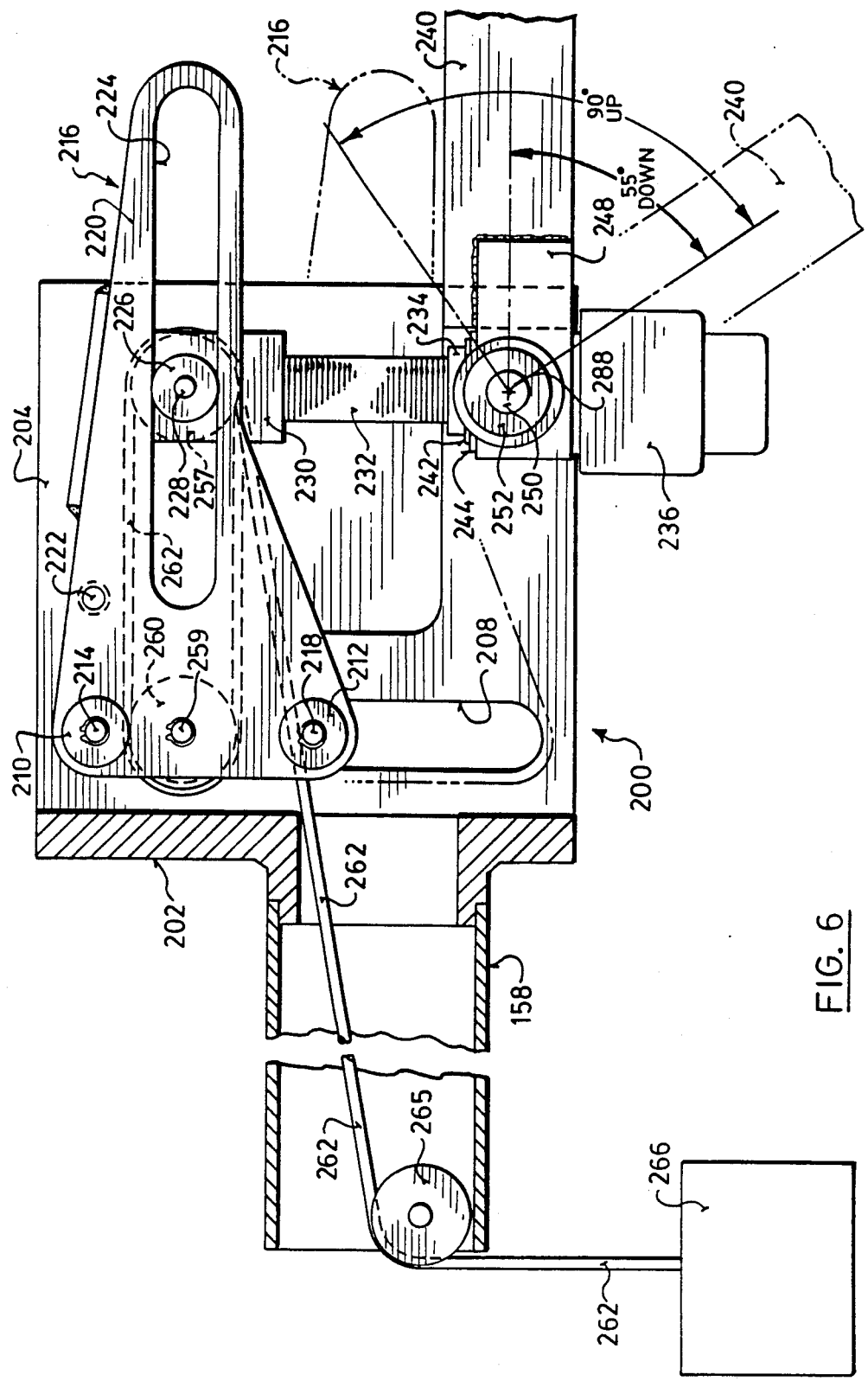
FIG. 6 is a vertical sectional view through an angulation compensation device forming part of this invention.

With reference to FIG. 6, there is shown an angulation compensation device adapted to be fixed to the end of the primary arm 158. The device is generally shown at 200, and includes a back wall 202, and two side walls 204 and 206 (see FIG. 7). The side walls 204 and 206 define aligned oval openings 208 which are oriented vertically and are located adjacent the back wall 202. Vertically slidable in the openings 208 are an upper pair of rollers 210 and a lower pair of rollers 212. The upper pair of rollers 210 are supported on a shaft 214 fixed with respect to a carriage 216 adapted to reciprocate vertically. The lower pair of rollers 212 rotate about a shaft 218 which is also fixed with respect to the carriage 216, directly beneath the shaft 214 and spaced therefrom.

The carriage 216 comprises two plate members 220 which are oriented vertically and spaced apart by virtue of the shafts 214 and 218, and also by a separate spacer shaft 222. The plate members 220 are identical, and define horizontal oval slots 224 which are in horizontal alignment, and in which a pair of rollers 226 is adapted to reciprocate. The rollers 226 are journaled on a shaft 228, the shaft 228 being supported by a U-shaped yoke 230, best seen in FIG. 8. The yoke 230 is fixed to the upper end of a threaded shaft 232 which does not rotate, but which is capable of undergoing axial movement.

Figure 8:
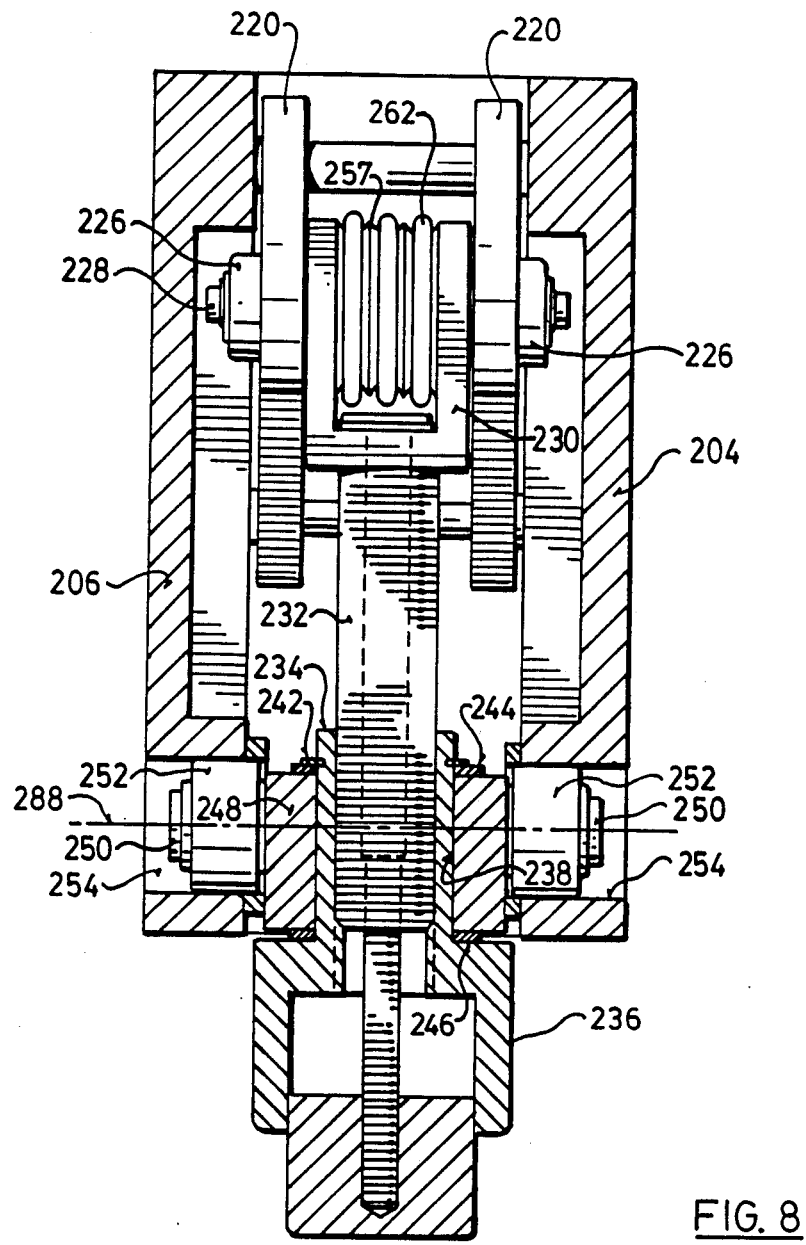
FIG. 8 is a vertical cross section through the device of FIG. 6.

Referring to FIG. 8, the shaft 232 threadably engages an upper cylindrical portion 234 projecting integrally from a knob 236. The cylindrical portion 234 has a smooth, cylindrical outer surface which is received with close tolerance in a bore 238 which is provided in a swing arm 240. In FIG. 6, the swing arm 240 projects rightwardly away from its connection with the threaded shaft 232. The knob 236 and the portion 234 are retained by virtue of a retaining ring 242 and two thrust washers 244 and 246 in such a way that the portion 234 cannot move axially with respect to the swing arm 240. However, the knob 236 can be used to rotate the portion 234 about its axis, and the threaded engagement with the shaft 232 will mean that rotation of the portion 234 will cause the shaft 232 to move axially.

The swing arm 240 includes a block 248 in which the bore 238 is actually located, and further includes the main arm portion which is welded to the block 248.

Extending toward the side of the block 248, as best seen in FIG. 8, are two stub shafts 250 which are journaled in two bearings 252 which are in turn held in horizontal bores 254 in the side walls 204 and 206.

Returning to the upper portion of FIG. 8, it will be seen that the shaft 228 carries, between the arms of the yoke 230, three pulleys 257.

Looking at the left of FIG. 6, there is provided a further shaft 259 on which three further pulleys 260 are provided. Wrapped around the pulleys 257 and 260, in the manner of a block-and-tackle, is a cable 262 which has one end attached to the carriage 216 (not shown), and has the other end extending leftwardly (in FIGS. 6 and 7) into the hollow interior of the extension arm 158, and ultimately around a further pulley 265, from where it drops down to support a weight 266.

It is to be emphasized that the weight 266 is only one of several means which can be utilized to provide a substantially constant force acting on the end of the cable 262. Another such means would be constituted by "constant force springs", as they are referred to in the industry. These devices are well known, and provide a substantially constant force over a given extension length. Yet another mechanism for providing a substantially constant force would be an atmospheric counterbalance, in which a piston slides in a cylinder, the piston being exposed to atmospheric pressure at one end and to a substantial or near vacuum at the other end. Depending on design, the piston of the atmospheric counterbalance could be connected to pull directly on the shaft 228, so long as the direction of the pull could be arranged to be unvarying.

Attention is now directed to FIGS. 8 and 9, which show a braking or friction mechanism adapted to stall or freeze the block-and-tackle mechanism at any given setting. The shaft 232 has an internal bore 270 which communicates with a smaller-diameter internal threaded bore 272 at the bottom. Into the threaded bore 272 is screwed a threaded shaft 274 to which a freeze knob 276 is fixed by a pin 278, the pin passing through the knob 276 and the shaft 274. At the top, the shaft 274 has a reduced-diameter integral pin 280 which rotatably engages a bore at the bottom of a cylinder 282 which has an integral outward flange 284 resting at the bottom of the area defined between the two arms of the yoke 230. The flange 284 supports a pad 286 of friction material. It will be appreciated by referring to FIGS. 8 and 9 that rotation of the freeze knob 276 will urge the pad 286 upwardly against the wraps of the cable 262 trained around the pulleys 257, thus freezing the cable in any given position.

Referring now to FIG. 6, it will be seen that the swing arm 240 is adapted to rotate in the vertical plane about an axis 288 representing the centre of the shaft 250. At the rightward end of the swing arm 240 is a flex head 290 similar to that described previously in this specification.

It will further be appreciated that the leftward pull exerted at the top of the shaft 232 due to the block-and-tackle arrangement at the cable 262 will tend to counterbalance the downward force exerted by any weight, such as a monitor 292 hung downwardly from the flex head 290 at the rightward end of the swing arm 240. In the embodiment illustrated, the block-and-tackle has a mechanical advantage factor of six, so that, when the swing arm 240 is horizontal, the leftward force at the top of the shaft 232 exerted by the the block-and-tackle will be six times the value of the weight 266. This in turn would mean that, if the swing arm 240 were six times as long as the shaft 232 measurement between the axis 288 and the centre of the shaft 228, the weight 266 could have approximately the same value as the weight of the monitor or other piece of apparatus 292. For different monitor weights, or for different lengths of the swing arm 240, the effective length of the shaft 232 can be adjusted by rotating the knob 236 in order to maintain the counterbalancing effect.

It will further be understood by those skilled in the art that the weight 266 could be replaced by a constant-force spring. Several designs of such springs are already known and available on the market. Such a constant-force spring could be mounted within the primary arm 158.

It will further be understood, from an inspection of FIG. 6, that as the swing arm 240 pivots downwardly in the vertical plane in a clockwise direction, the carriage 216 will be moved downwardly along the track represented by the oval openings 208, thus maintaining the axis of the shaft 259 and the axis of the shaft 228 in the same horizontal plane. This is important in order to ensure that the horizontally leftward force on the shaft 228, which tends to compensate the weight of the monitor 292 or other piece of equipment, will remain constant. Further, it will be understood that, even though the leftward horizontal force on the axis 228 remains constant, the torque tending to restore the swing arm 240 to a horizontal position decreases in proportion to the cosine of the angle between the horizontal and the axis of the swing arm 240, due to the fact that the vertical distance between a horizontal plane through the axis 288 and a horizontal plane through the axis of the shaft 228 decreases according to the same proportion. However, this decreased torque is precisely what is required for compensating the weight of the monitor or other piece of apparatus 292, since the torque exerted on the arm 240 by the monitor 292 is also decreasing in the same proportion due to the fact that the horizontal distance between the axis 288 and a vertical plane containing the central axis of the flex head 290 is also decreasing proportionately to the cosine of the angle already defined. The precise match between the torques would be essential in an idealized "frictionless" situation, or if the friction were reduced to a minimum by the use of rollers sliding on ideally smooth surfaces. However, a specific amount of friction can be deliberately built in to the apparatus, such that small divergences between the torques can be accommodated.

Figure 11:
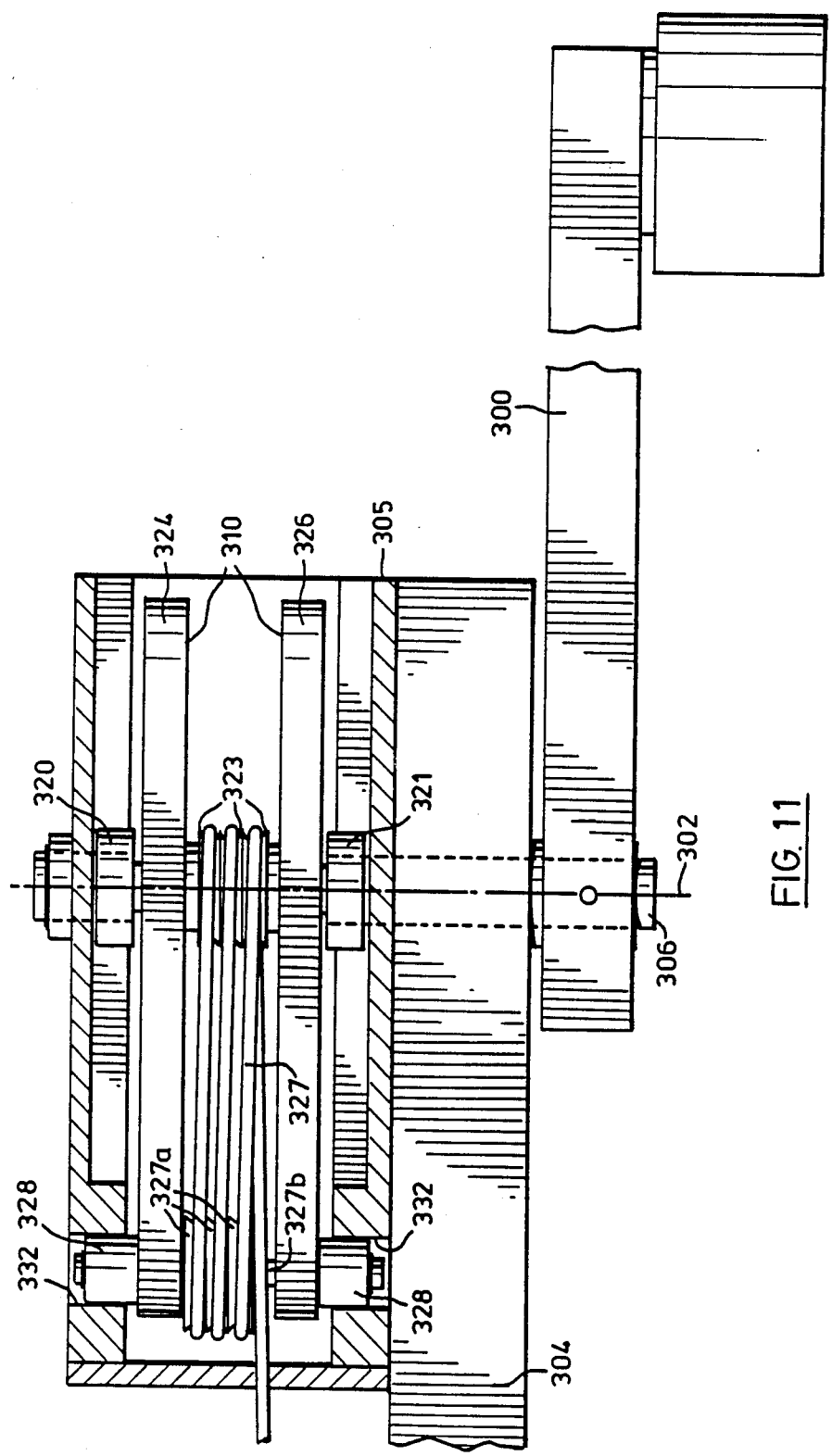
FIG. 11 is a plan view of the device of FIG. 10.
Figure 12:
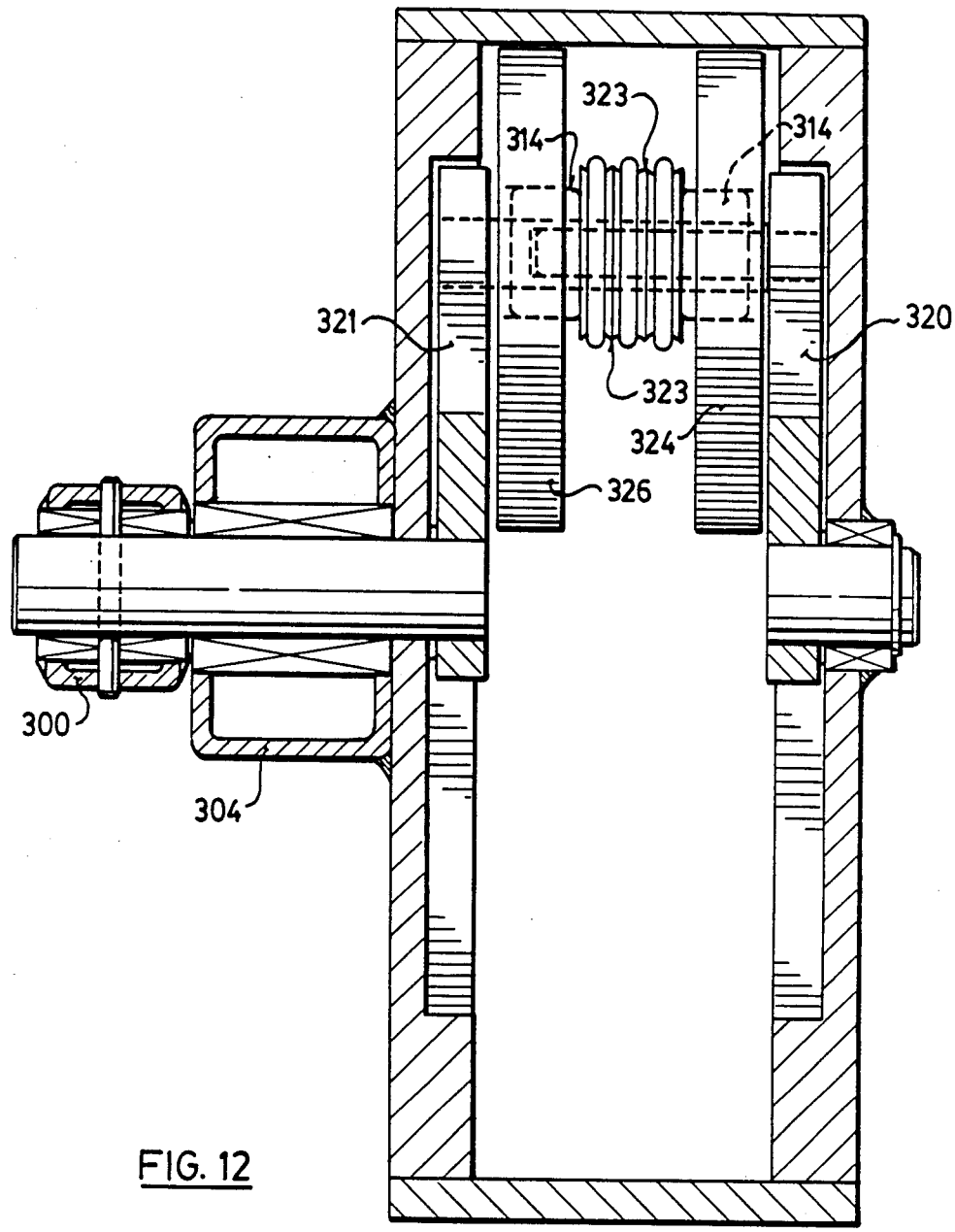
FIG. 12 is a cross-sectional view through the device of FIG. 10.

Attention is now directed to FIGS. 10 and 11, which show a variation embodiment of this invention, in which a swing arm 300 is capable of 360° rotation about a central axis 302 which is fixed with respect to an extension arm 304 analogous to the arm 158. More specifically, the swing arm 300 is mounted outside of a frame 305, and rotates about a shaft 306 of which 302 is the axis. In the case of the embodiment of FIGS. 10 and 11, the carriage 310 is adapted to move through a greater distance, in order to allow a crank 312, which is fixed with respect to the swing arm 300 and projects at right angles therefrom, to rotate fully through 360°. The crank 312 carries a roller 314 which engages horizontal, oval slots 316 which are long enough to permit rotation through 360°. Again, the crank 312 comprises two upstanding members 320 and 321 (see FIG. 11), and the shaft 306 carries three pulleys 323 between two plate members 324 and 326 which make up the carriage 310. A cable 327 wraps around the pulleys 323 and three other pulleys 327a on a shaft 327b in the manner of a block and tackle, similar to the arrangement of FIGS. 6, 7 and 8.

The carriage 310 supports two pairs of rollers 328 and 330 for longitudinal vertical reciprocation in oval openings 332.

Figure 7:
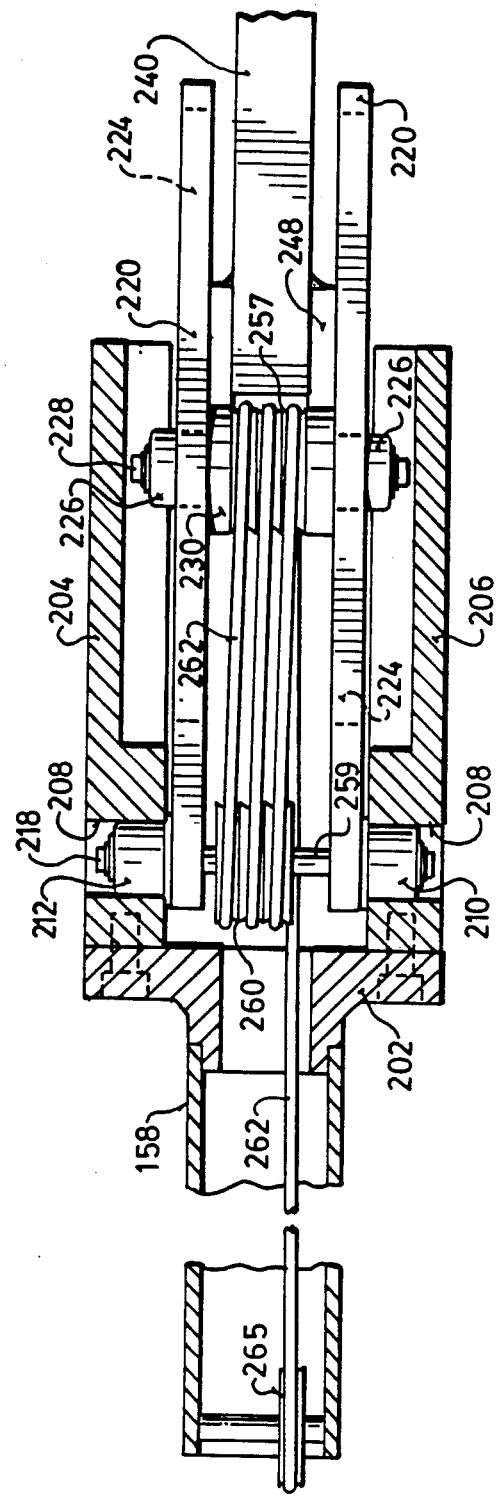
FIG. 7 is a horizontal section through the device of FIG. 6.

From what has been described, it will be evident that the basic compensation and counterbalance mechanism for the embodiment of FIGS. 10 and 11 operates on the same principle as that for the embodiment of FIGS. 6 and 7. Accordingly, no further detailed description is required.

Figure 13:
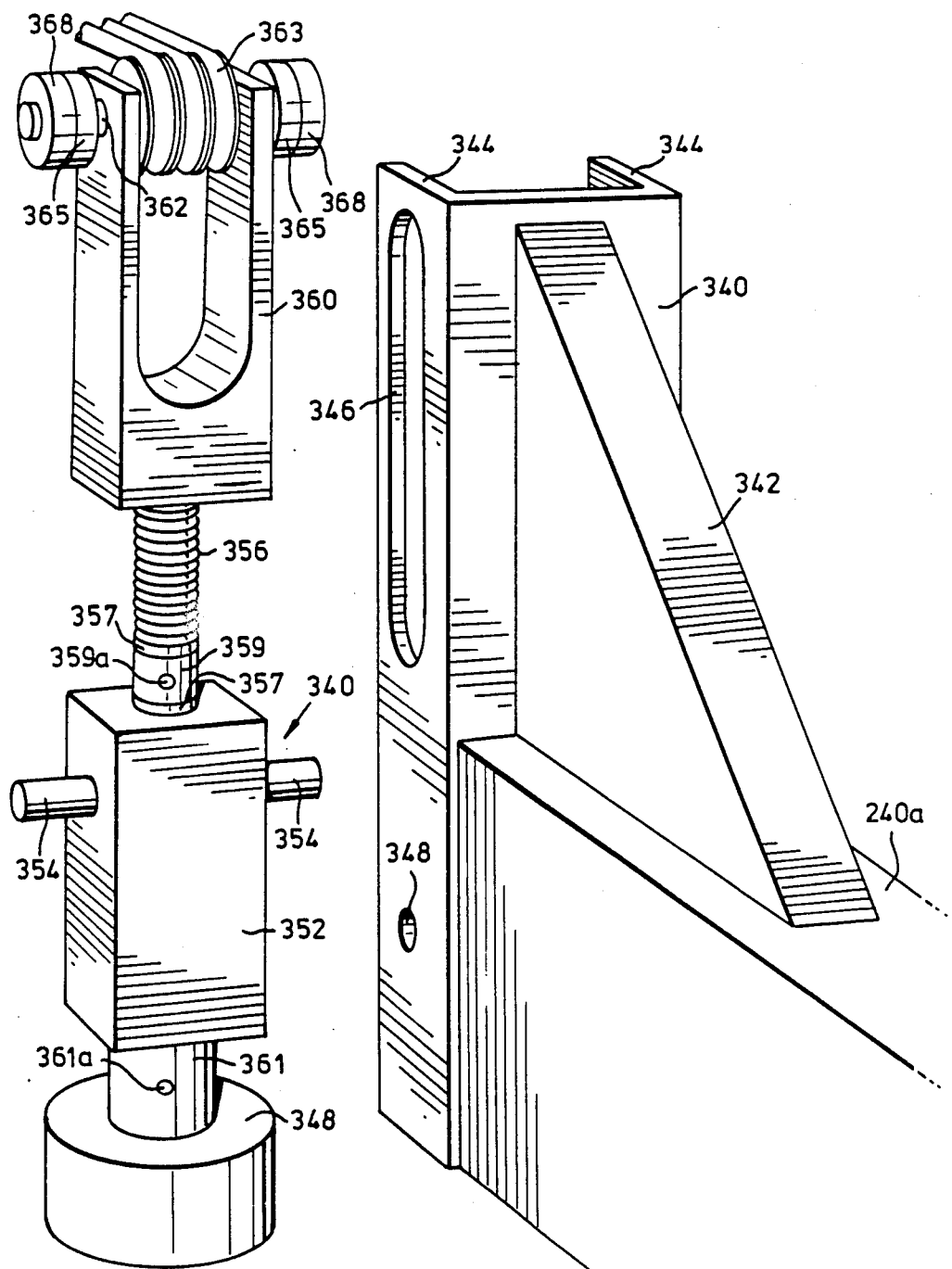
FIG. 13 is an exploded, perspective view of an alternative construction for use with the device of FIG. 6.

Attention is now directed to FIG. 13, which shows a variation for the structure best seen in FIG. 8, i.e. that which changes the distance between the axis 288 and the axis of the shaft 228. It will be appreciated that, due to the force exerted by the block-and-tackle, there may be a tendency, under heavy loads, for the threads of the shaft 232 to bind, thus making it difficult to rotate the knob 236.

The mechanism of FIG. 13 overcomes this difficulty by providing a fixed crank 340 securely braced by a bracket 342 to a swing arm 240a. The crank 340 has a C-shaped cross section, providing two arms 344 of the section, each arm having an elongated, oval slot 346 (only one visible). Below the openings 346 are provided two bores 348 in alignment between the arms 344. To the left in FIG. 13 is shown an assembly 350 which includes a block 352 having trunions 354 adapted to register in the bores 348, with the block 352 between the arms 344. A shaft 356 extends through a non-threaded bore centrally of the block 352, such that it can rotate with respect to the block 352 without engaging the same. There is provided a thrust washer 357 above the block 352, and another (not visible) below it. A jam nut 359 is secured to the shaft 356 by a set screw 359a. A knob 358 has an integral shaft 361 by which it is locked to the shaft 356 using a set screw 361a. The jam nut 359 and the knob 358 hold the shaft 356 axially in place with respect to the block 352, while allowing for rotation of the shaft 356 with respect to the block 352. The shaft 356 is threaded into a correspondingly threaded bore of a yoke 360, such that rotation of the shaft 356 causes the yoke to move longitudinally toward and away from the block 352. At the upper end of the yoke 360 is supported a shaft 362 which in turn supports pulleys 363 between the arms of the yoke 360, and outboard of the yoke 360 the shaft 362 supports two pulleys at either end. A first inner pair of pulleys 365 is adapted to engage the arms 344 of the crank 340, specifically in the openings 346. An outer pair 368 of rollers engages the slots 224 in the carriage 216. This arrangement allows the crank 340 to take the torque load exerted by the block-and-tackle, but leaves the mechanism 350 free of any torque so that the mechanism 350 can simply adjust the distance between the shaft 362 and the trunions 354. The trunions 354, of course, correspond to the shaft 250 in the embodiment shown in FIG. 6, and could be provided with suitable bearings to reduce friction.

Attention is now directed to FIG. 14, which schematically shows a swing arm 400 consisting of a first member 402 pivoted at the axis 404 with respect to a fixed body, for example one end of a slide arm. The swing arm 400 further includes a first slidable member 406 and a second slidable member 408, both being slidable with respect to the fixed member 402. The slidable members 406 and 408 slide longitudinally along the member 402, utilizing guide means which have not been represented in this schematic figure. Fixedly projecting from the first member 402 is a yoke 410 through which an elongated threaded member 412 extends. The connection between the yoke 410 and the threaded member 412 is such that the threaded member 412 can rotate with respect to the yoke 410, but cannot move axially with respect thereto.

Extending from the first slidable member 406 is a flange 414 having a threaded bore through which the threaded member 412 passes. A similar flange 416 extends from the second slidable member 408, and the threaded member 412 likewise passes through a threaded bore in the flange 416. However, the direction and pitch of the threads engaging the two threaded bores in the flanges 414 and 416 are selected to be such that, when the threaded member 412 is rotated, for example by rotating the knob 418 manually, the slidable members 406 and 408 move toward each other or away from each other in a proportionate sense. More specifically, it can be seen that the rightward end of the slidable member 406 supports a weight 420, which is intended to represent a piece of equipment or other apparatus being suspended in the gravitational field by the swing arm 400. At the leftward end of the slidable member 408 is a block and tackle arrangement 422, similar to that described earlier. A cable 424 has one of it ends connected to a constant force means represented by the arrow 426. As the knob 418 is rotated in the direction which causes the rightward end of the slidable member 406 to move leftwardly toward the pivot location 404, at the same time the leftward end of the second slidable member 408 moves rightwardly toward the pivot location 404, drawing the entire block and tackle mechanism 422 to the right along with it, in such a way that the proportion between the distance A and the distance B remains substantially constant. The same constancy continues when the slidable members 406 and 408 are moving away from each other.

It is to be pointed out that the threaded member 412 is not the only mechanism that could be utilized to ensure this proportionate movement. For example, a lever system could be devised, or alternatively a rack and pinion mechanism could be utilized.

Additionally, it will be understood that the threaded member 412 could be rotated by a reversible electric motor, so that if desired, the length change could be done remotely.

While two embodiments of this invention have been illustrated in the accompanying drawings and described hereinabove, it will be evident to those skilled in the art that departures and modifications may be made therein without departing from the essence of the invention.

The embodiments of the invention in which an exclusive property or privilege is claimed are defined as follows:

1. An apparatus for suspending an article for movement in the gravitational field, comprising:
    hanger means adapted to be fixed in place,
    an axle member below and secured to the hanger means,
    a rotor portion mounted on the axle member for rotation about a vertical axis,
    a housing connected to the rotor portion and defining a horizontal passageway offset with respect to said vertical axis and entirely outside the axle member,
    a slide arm in said passageway, and
    guide means for guiding the slide arm within said passageway,
    the axle member being hollow and containing gas lines and electrical conduits, the apparatus including, beneath the axle portion, a manifold containing at least one coupling for the distribution of gas, and at least one electrical outlet.

2. The invention claimed in claim 1, in which said guide means includes two spaced-apart pairs of rollers, the two rollers of each pair being vertically separated so that the slide arm passes between them.

3. The invention claimed in claim 1, in which the housing and the rotor portion are integral.

4. The invention claimed in claim 1, in which the hollow axle member defines a central, three-lobed passage for the gas lines and the electrical conduits.

5. The invention claimed in claim 1, in which the said axle member is adapted to support beneath it and above the manifold a further hollow axle member with a further rotor portion mounted thereon for rotation about the same vertical axis, the axle members being in communication internally, a further housing portion connected to the further rotor poriton and defining a further horizontal passageway offset with respect to said vertical axis, and entirely outside the further axle member, with a further slide arm in said further passageway, and further guide means for guiding the further slide arm within the further pasageway.

6. The invention claimed in claim 1, in which the slide arm is hollow and contains electrical wires by which suspended equipment can be powered, said wires being connected through said housing to a conduit loop located between the axle member and the housing, the loop being in turn connected to said electrical conduits within the hollow axle member.

7. The invention claimed in claim 1, further incorporating a mechanism for counterbalancing the weight of the article while allowing the article to be displaced vertically, said mechanism including a swing arm pivoted near one of its ends to the slide arm and having near its other end a support means for supporting said article, first means providing a substantially constant force with respect to said slide arm, the force being exerted along a direction which remains fixed with respect to the slide arm, and second means applying said force to the swing arm at a given location spaced from said horizontal axis, in such a way as to maintain a substantially constant proportion between (a) the horizontal distance between the horizontal axis and a vertical line through the article, and (b) the distance from said horizontal axis to a line parallel to said direction and passing through the said location, the latter distance being taken normal to said last-mentioned line.

8. The invention claimed in claim 7, in which said last-mentioned line is horizontal.

9. The invention claimed in claim 7, in which said first means is a block and tackle assembly having a plurality of pulleys on each of two axles, with a cable wrapped around the pulleys, one of the axles being mounted in fixed relation with respect to the swing arm, the other of the axles being mounted to a carriage adapted to reciprocate vertically with respect to the slide arm, the carriage having cam means for maintaining the axes of the two axles in horizontal alignment, one end of the able being secured at a fixed place on the apparatus, the other end of the cable being attached to a means for exerting a substantially constant force.

10. The invention claimed in claim 9, in which the swing arm includes a flange projecting at right angles from its main extent, said one axle being mounted to said flange in a position such that a line from the axis of said one axle to said horizontal axis on the first member is perpendicular to the main direction in which said swing arm extends.

11. The invention claimed in claim 9, which further includes a braking means by which to frictionally stall the movement of said cable at any desired position of the block and tackle assembly, the braking means including a manually rotable threaded member adapted to urge a friction pad against the cable.

12. The invention claimed in claim 10, in which said one axle is mounted to said flange in such a way that the true distance between the horizontal axis and the axis of said one axle can be selectively adjusted.

13. An apparatus for suspending an article within the earth's gravitational field, comprising:
hanger means adapted to be fixed in place,
a plurality of hollow axle means connected one below the other in vertical alignment to provide a continuous central vertical passage linking all axle members, the passage being adapted to house gas lines and electrical conduits, the topmost axle member being secured to the hanger means,
a rotor portion mounted on each axle member for rotation thereabout,
a housing connected to each rotor portion and defining a horizontal passageway offset with respect to the rotary axis of the rotor portion and lying entirely outside the respective hollow axle member,
a slide arm in each passageway, and
guide means in each passageway for guide the respective slide arm within its passageway
each axle member having at least one lateral opening for allowing power cable access to the respective slide arm.

14. The invention claimed in claim 13, in which all of the rotor portions rotate about a common vertical axis.

15. The invention claimed in claim 13, in which each said guide means includes two spaced-apart pairs of rollers, the two rollers of each pair being vertically separated so that the respective slide arm passes between them.

16. The invention claimed in claim 13, in which each slide arm is hollow and contains electrical wires by which suspended equipment can be powered, said wires being connected through the respective housing to a conduit loop located between the respective axle member and its housing, the loop being a turn connected to said electrical conduits within the hollow axle members.

17. An apparatus for counterbalancing the weight of an article in the gravitational field while allowing the article to be displaced vertically, comprising:
a first member defining a horizontal axis,
a swing arm pivoted adjacent one end about said horizontal axis and having support means adjacent the other end for supporting said article,
stretchable means having two ends and providing a substantially constant force drawing said ends together, and
means applying said force to the swing arm at a given location spaced from said horizontal axis, in such a way as to maintain a substantially constant proportion between (a) the horizontal distance between the axis and a vertical line through the article, and (b) the distance from said axis to a line parallel to the direction of said force and passing through the said location, the latter distance being taken normal to said last-mentioned line.

18. The invention claimed in claim 17, in which said last-mentioned line is horizontal, and in which the force is exerted along a direction which remains fixed with respect to the first member.

19. The invention claimed in claim 17, in which said stretchable means is a block and tackle assembly having a plurality of pulleys on each of two axles, with a cable wrapped around the pulleys, one of the axles being mounted in fixed relation with respect to the swing arm, the other of the axles being mounted to a carriage adapted to reciprocate vertically with respect to said first member, the carriage having cam means for maintaining the axes of the two axles in horizontal alignment, so that the direction of the force is horizontal, one end of the cables being secured at a fixed place on the apparatus, the other end of the cable being attached to a means for exerting a substantially constant force.

20. The invention claimed in claim 19, in which the swing arm includes a flange projecting at right angles from its main extent, said one axle being mounted to said flange in a position such that a line from the axis of said one axle to said horizontal axis on the first member is perpendicular to the main direction in which the swing arm extends.

21. The invention claimed in claim 17, in which the swing arm is capable of rotation about said horizontal axis through 360 degrees.

22. The invention claim in claim 20, in which the swing arm is capable of rotation about said horizontal axis through 360 degrees.

23. The invention claimed in claim 19, which further includes a braking means by which to frictionally stall the movement of said cable at any desired position of the block and tackle assembly.

24. The invention claimed in claim 23, in which the braking means includes a manually rotatable threaded member adapted to urge a friction pad against the cable.

25. The invention claimed in claim 20, in which said one axle is mounted to said flange in such a way that the true distance between the horizontal axis and the axis of said one axle can be selectively adjusted.

26. The invention claimed in claim 19, in which said means for exerting a substantially constant force is a weight suspended in the gravitational field.

27. The invention claimed in claim 19, in which said means for exerting a substantially constant force includes at least one constant force spring.

28. The invention claimed in claim 14, in which the distance between the horizontal axis and the means at the other end of the swing arm for supporting the article is adjustable, the true distance from the horizontal axis to the said location being also adjustable, the apparatus including means for simultaneously adjusting these two distances in such a way that they substantially retain the same proportion regardless of the adjustment.

29. The invention claimed in claim 28, in which the means for simultaneously adjusting includes a manually rotatable threaded member.

* * * * *